United States Patent [19]
Thompson

[11] Patent Number: 5,836,532
[45] Date of Patent: Nov. 17, 1998

[54] SYSTEM AND METHOD FOR ON-LINE MISSING/GAINED FILAMENT DETECTION

[75] Inventor: Dewey Edwin Thompson, Signal Mountain, Tenn.

[73] Assignee: E. I. du Pont de Nemours and Company, Wilmington, Del.

[21] Appl. No.: 760,977

[22] Filed: Dec. 5, 1996

[51] Int. Cl.$^6$ .......... B65H 54/02; B65H 63/02; G06G 7/64
[52] U.S. Cl. .......... 242/35.5 R; 242/40; 242/18 G; 242/36; 364/470.1; 364/470.15
[58] Field of Search .......... 242/36, 35.5 R, 242/38, 40, 18 G; 364/469.05, 470.1, 470.14, 470.15

[56] References Cited

U.S. PATENT DOCUMENTS

| | | | |
|---|---|---|---|
| 4,007,883 | 2/1977 | Isoard | 242/35.5 R |
| 4,269,368 | 5/1981 | Rapp et al. | |
| 4,351,494 | 9/1982 | Schippers et al. | 242/36 X |
| 4,715,548 | 12/1987 | Miyake et al. | 242/36 X |
| 4,805,844 | 2/1989 | Hermanns et al. | 242/36 X |
| 4,828,191 | 5/1989 | Ruge et al. | 242/36 X |
| 5,023,820 | 6/1991 | Baum | 364/496.05 X |
| 5,142,159 | 8/1992 | Veit et al. | |
| 5,399,815 | 3/1995 | Ballarati | |
| 5,446,951 | 9/1995 | Takeuchi et al. | |

FOREIGN PATENT DOCUMENTS

| | | |
|---|---|---|
| 0 202 624 | 11/1986 | European Pat. Off. |
| 0 618 166 A1 | 10/1994 | European Pat. Off. |

*Primary Examiner*—Michael Mansen

[57] ABSTRACT

An on-line system and method provides for monitoring the build up of yarn package diameter which detects winding defects, including missing or gained filaments, in multifilamentary yarn spinning processes. The system and method derive and compare yarn package denier for several yarn packages wound on a common winding apparatus. Diameter ranges are used to divide a yarn package into various measurement zones. Denier measurements are derived for each zone from two on-line, real-time inputs: yarn package speed and time to traverse the specified zone. Comparison of denier for diverse packages being simultaneously wound on one winding apparatus are compare to each other and determined to be within a specified tolerance. The apparatus operator is notified of out of tolerance measurements so that remedial action may be taken. The system also provides for constant and periodic updating of the denier measurement algorithm to account for process variations.

23 Claims, 9 Drawing Sheets

SYSTEM AND METHOD FOR ON-LINE MISSING/GAINED FILAMENT DETECTION

FIELD OF THE INVENTION

This invention relates to winding multifilamentary material and more specifically to a method and system for on-line monitoring of the multifilamentary material as it is being wound.

BACKGROUND OF THE INVENTION

Man-made fiber manufacturing technology relies on yarn winding processes to form packages of yarn. The yarns are formed by extruding polymers, melt spinning for example, through capillaries in a spinneret to form multiple filaments. These filaments are quenched and combined into a multifilament yarn (called a threadline) which is subsequently wound onto packages. Many multifilament spinning processes depend upon forming many filaments from a multi-capillary spinneret and converging these filaments into 2 or more threadlines. Subsequently, these threadlines are wound on neighboring winding chucks to form the multifilament yarn package. The finished yarn packages are used in many applications including yarn texturing, fabric knitting or weaving processes where yarn strength and uniformity is critical.

During the spinning process a fault during multiple threadline winding can occur known as "missing or gained filament defect". Missing or gained filaments occur when a filament breaks and does not converge into the yarn bundle or migrates from one threadline to another threadline closely spaced on the same spinning position and sharing a common winding apparatus.

For example, a spinneret with 40 capillaries may be used to spin 40 filaments which are then converged into 4 threadlines of 10 filaments each and wound up into 4 yarn packages on a single common winding apparatus. If a single filament breaks and does not converge into any of the yarn packages, there would be 3 yarn packages of 10 filament yarns and one yarn package of a 9 filament yarn. The linear density of the 9 filament yarn would be reduced by 10 per cent and most likely unsuitable for the same usage as intended for the 10 filament yarn packages. Alternately, a filament may migrate from one threadline to another. The yield of "good" 10 filament yarn packages is then even less. Here one yarn package gains a filament and converges to an 11 filament yarn and one yarn package looses a filament and converges to a 9 filament yarn. Of course, variations of the two faults are possible, broken filaments with migration etc.

Perhaps an even more insidious variation on missing and gained is the disappearing missing and gained filament. It is known in the art of winding multifilamentary yarn materials from multiple closely spaced threadlines to have a filament migrate back and forth between a pair of yarn packages. This is called "come and go" missing and gained. These types of come and go defects have been a long standing problem in the art.

Post wind deniering of the packages is sometimes able to uncover simple missing and simple gained filaments, and allow appropriate disposition of the defective package(s). However, weighing or differential weighing is not necessarily precise enough to uncover come and go filament windings buried deeply in the yarn package. Such defective packages have potential for disastrous consequences when used in certain weaving and knitting processes.

The presence of missing and gained filament faults are recognized as a serious quality problem in yarn spinning and causes waste and reduced productivity. Deniering, or measuring the liner density of yarn packages by weight, where linear density may be expressed as yarn denier (1 denier=1 gram per 9000 yards) or yarn deciTex (1 deciTex=1 gram per 10000 meters), has been practiced for many years as an off-line remedy to detect defective yarn packages. Deniering by direct weighing or differential weighing off-line allow post-spinning disposition of missing or gained filament yarn packages. However, off-line deniering methods do not present the opportunity for remedial action to be taken during winding thus allowing the benefit of potentially significant cost savings through improved quality assurance and control.

"On-line" means to detect missing or gained filaments in real-time and allow remedial action to be taken to avoid winding a full defective package and otherwise identify a defective package not suited for critical downstream yarn processing. Some known on-line methods disclose on-line means to classify wound yarn packages within a range of specific package weights and external diameters, however, missing or gained filaments remain undetected.

SUMMARY OF THE INVENTION

The present invention overcomes the above described deficiencies in the prior art by providing a system and method for calculating and monitoring on-line, in real time, the linear density, or denier, of a yarn package.

In one illustrative embodiment, the method and apparatus of the present invention provide for using a microprocessor to monitor the linear density of at least one yarn package where predetermined process parameters are input to the microprocessor, including a tolerance range and at least one diameter range. The rotation speed of each yarn package and a measured time interval required to wind a yarn package through the specified diameter range are measured and provided to the microprocessor. A denier or linear density is calculated using the rotation speed, time interval input values and the process parameters. The calculated denier values are then compared to the specified tolerance range, with results of the tolerance comparison displayed.

Other advantages and features of the present invention will become apparent in view of the following detailed description of the illustrative embodiment.

DETAILED DESCRIPTION OF THE INVENTION

Briefly, the system and method of the present invention provide for on-line, real-time, yarn package denier measurement to determine winding deviations which can result from, among other causes, missing and gained filaments.

A specified annular volume of yarn for a number of measurement zones is determined based on rotational speed of a winding yarn package and companion driveroll.

The specified annular volume is converted to a weight using a nominal yarn package density factor.

The elapsed time during which the yarn annular volume was wound is measured based on pulses from a rotating shaft encoder on the wind-up spindle. Since the true yarn speed can be derived from the driveroll speed 20 and helix angle, the true yarn length is then calculated.

A preliminary (raw) denier is calculated based on the definition of denier, weight in grams of 9000 meters of yarn. The final deniers are determined by normalizing preliminary deniers using the known total denier for the spinning position or station. The maximum and minimum package deniers are then determined for comparison with product release specifications and product dispositioned accordingly.

Each denier measurement zone within a yarn package and for each spindle has an individual calibration factor which is updated frequently. This calibration factor accounts for the day to day spinning dynamics or variability associated with that particular denier measurement.

Figure 1:
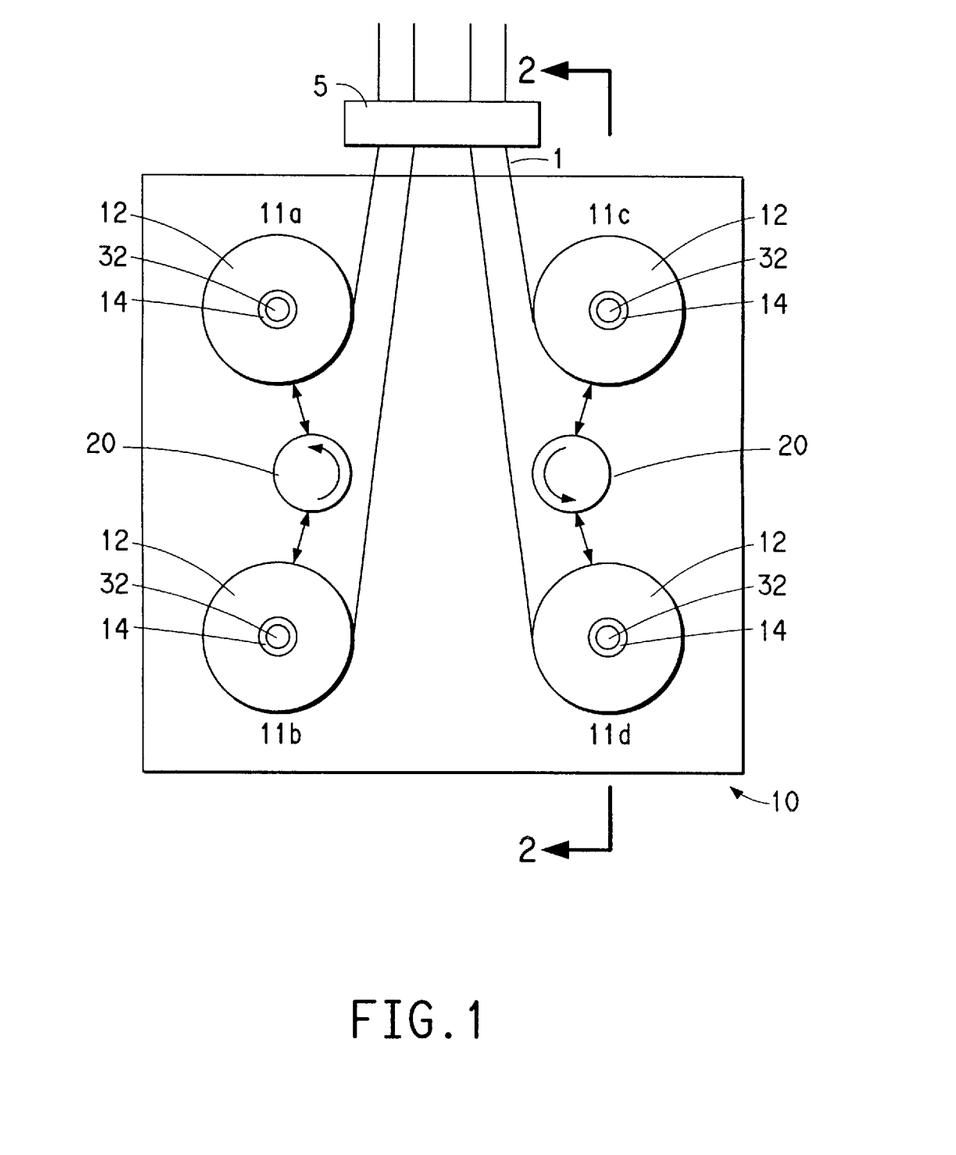
FIG. 1 is a front view of the winding apparatus of the illustrative embodiment of the present invention.

FIG. 1 illustrates a winding apparatus (or winding position) 10 used in a multifilamentary yarn spinning process to service a yarn spinning position (not shown). This spinning position provides one or more multifilament yarns or threadlines with paths defined by a yarn fanning guide 5 to winding position 10 used to wind each threadline into yarn package 12. In the illustrative embodiment shown, up to 4 yarn packages 12, each at a station 11a, 11b, 11c and 11d, can be wound simultaneously from yarn threadline 1 fed over guide 5.

Each yarn package 12 is formed around a yarn tube 14 which is securely mounted onto a freely rotatable spindle 32.

The outermost surface of each package 12 is in frictional contact with a solid driveroll 20, which is independently driven by a motor (not shown) of the winding apparatus to rotate at a precisely controlled pre-determined speed. The frictional contact causes the packages 12 to rotate at substantially the same surface speed as the driveroll 20, thus winding yarn onto the package 12. Frictional contact between the driveroll 20 and the packages 12 is maintained throughout the winding cycle (i.e., contact with the driveroll 20 is maintained with the growing diameter as the yarn is wound onto the tube) by virtue of spindles 32 being tensioned on a floating axis.

The yarn winds from package end to end, around and along the entire length of the tube, forming the yarn package 12 of a predetermined final diameter.

Figure 2:
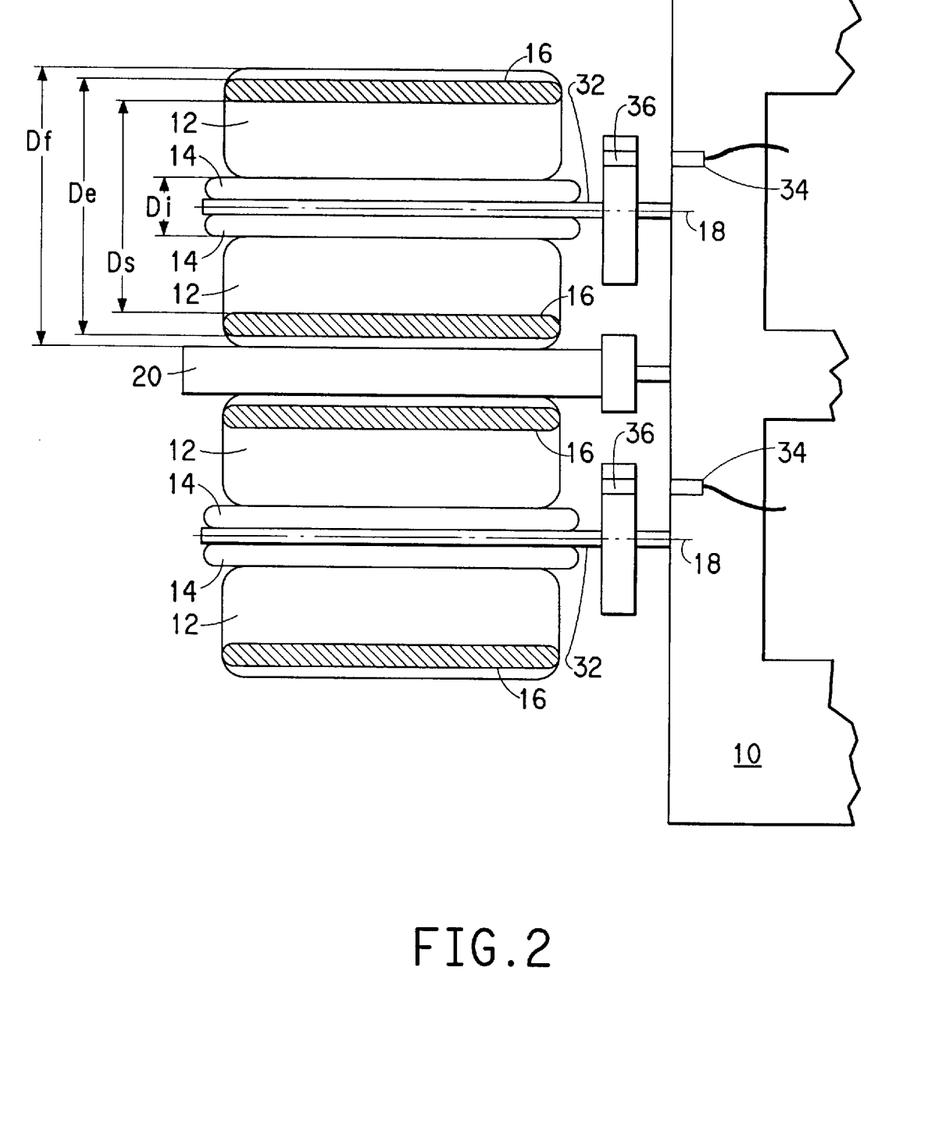
FIG. 2 is a section view of the winding apparatus of FIG. 1.

Referring now to FIG. 2, two yarn packages 12 at stations 11c and 11d (see FIG. 1) are shown in a section view, taken at section line 2 of FIG. 1.

Figure 6A:
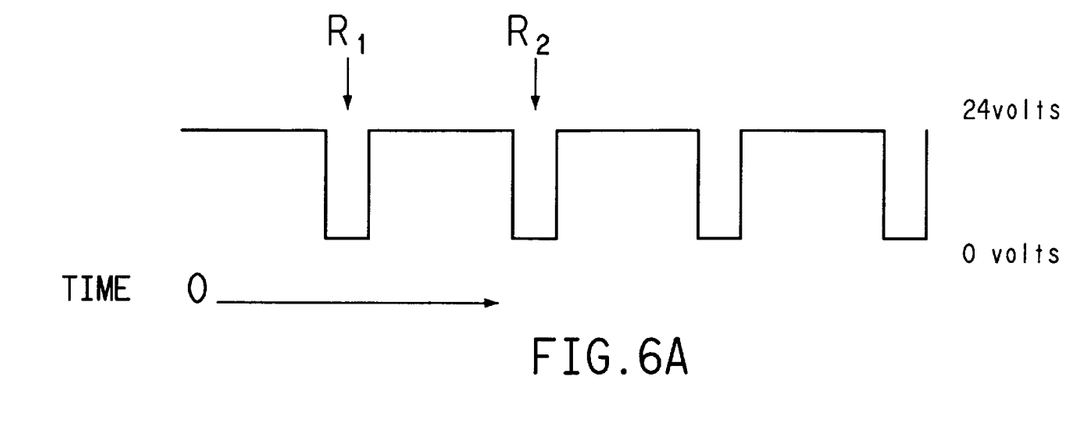
FIG. 6A illustrates the square wave pulse generated by the sensor/encoder apparatus of the illustrative embodiment of the present invention.

As shown in FIG. 2, spindle 32 is rotatable about an axis of rotation 18. The inner end of spindle 32 is fitted with an off-axis rotation encoder 36 whose passage is detected by a fixed sensor 34 for each complete rotation of spindle 32. In the illustrative embodiment, the off-axis rotation encoder 36 is a permanent magnet and the fixed sensor 34 is a Hall effect sensor. The operation of a magnet and Hall effect sensor to generate a pulse train (of a desired specific voltage) corresponding to the rotational speed (i.e., RPM) of the turning spindle will be understood by one of ordinary skill in the art. FIG. 6 depicts a 24 volt square wave pulse train generated by fixed sensor 34 in response to a turning spindle as used in the illustrative embodiment.

Figure 3:
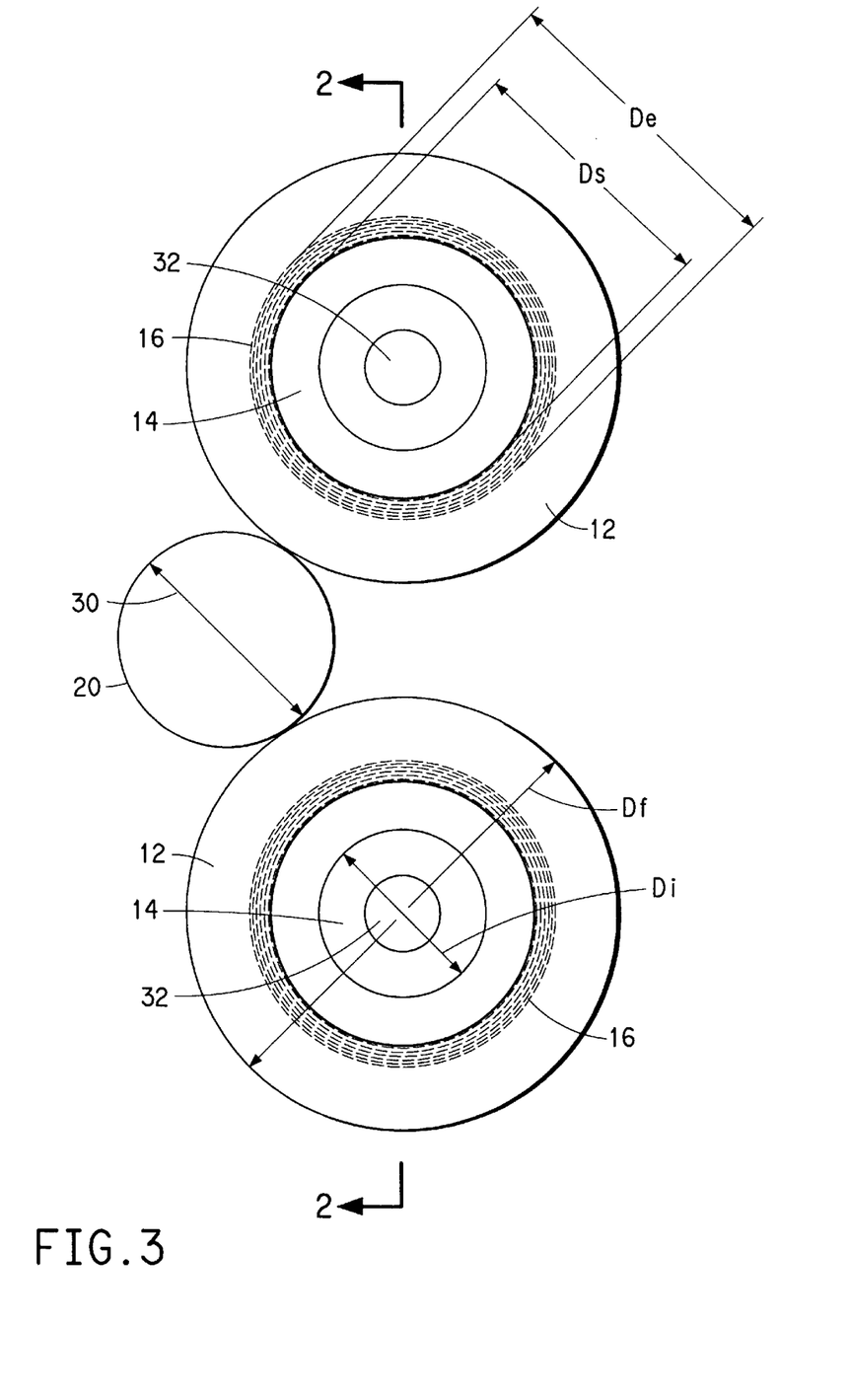
FIG. 3 is a detailed view of a portion of the apparatus of FIG. 1.

FIG. 3 shows an isolated view of the yarn packages 12 from stations 11c and 11d from FIG. 1 in further detail. As the yarn winds about core 14 uniformly, the diameter of the package will increase proportionately until a predetermined final diameter $D_f$ for the package is attained.

Each package 12 will have annular volume segments of yarn 16 in relation to the yarn tube core 14 for any set of differential diameters $D_s$ and $D_e$ within the initial and final diameters of the package, $D_i$ and $D_f$. Each set of differential diameters $D_s$ and $D_e$ forms a "radial measurement zone".

Figure 4:
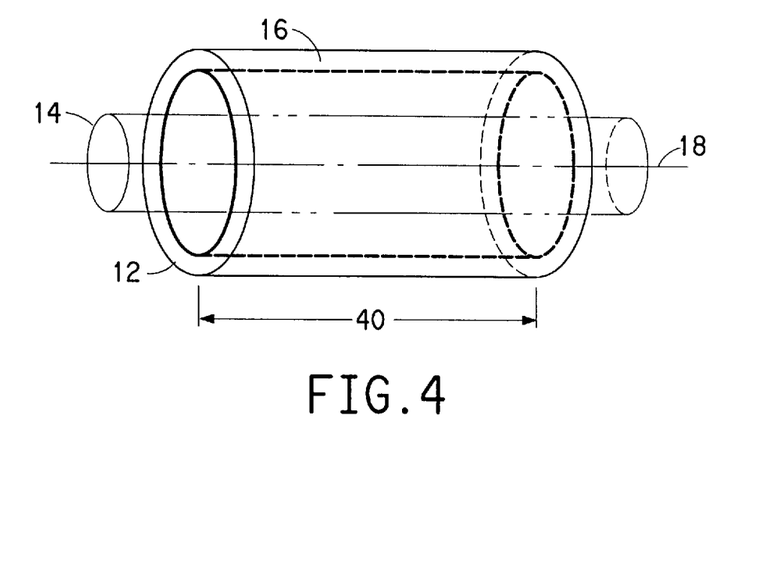
FIG. 4 is a perspective view of a portion of FIG. 2.

With reference to FIG. 4 (showing an isolated view of one yarn package 12), one yarn package 12 is shown with tube core 14 and axis 18. Each package 12 is wound end to end with yarn by the winding apparatus 10 (see FIG. 1) within a predetermined length 40 around core 14, the diameter of the package increasing as more yarn is wound. The yarn is wound about the tube at a specific helix angle so as to continuously traverse the entire length 40 as winding. One example annular volume segment of yarn 16 is shown about the axis 18.

Figure 5:
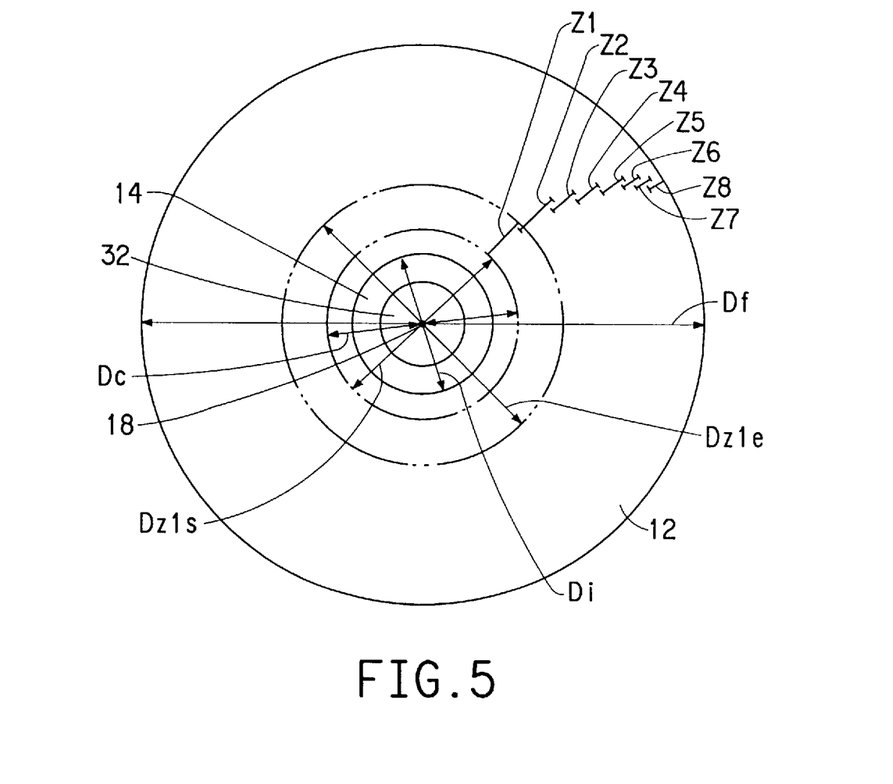
FIG. 5 is diagram of yarn package zones according to one embodiment of the present invention.

The method of the present invention, as will be described in greater detail below, utilizes several sets of differential diameters, or radial zones Z, as shown in FIG. 5 to determine missing or gained filaments which may occur during the winding process. Each zone $Z_n$, where n can be any desired number, has a start diameter of $D_{Zns}$ and an end diameter of $D_{Zne}$.

The characteristics of the individual zones will be selected based upon specific requirements established by the user.

For example, the number of zones to be applied must be determined. It is desirable that the zones overlap as in the illustrative embodiment so that there are no gaps in coverage for the entire diameter of the package (i.e., from $D_i$ through $D_f$). Likewise, the width of each zone will determine the amount of un-salvageable yarn when a denier anomaly is detected. A larger width results in potentially more cordage (or waste), and vice versa. In other words, if an anomaly is detected in a zone and the wind cycle is halted, the entire zone where the anomaly was detected can be stripped from the package and the remaining smaller diameter package can still receive a higher grade identification. The stripped yarn can receive some other degraded rating.

Start and end diameters $D_{Zns}$ and $D_{Zne}$ are selectable to be any diameters where $D_{Zns} < D_{Zne}$, as will be described in detail below. It is desirable to have a minimum diameter differential for the final zone to assure accurate calculation. If this final zone minimum diameter is not reached, the missing/gained filament detection results may not be accurate for that zone.

The illustrative embodiment uses eight overlapping zones $Z_1$–$Z_8$ to span the diameter of the yarn package 12. In this illustrative embodiment, the start diameter of the first zone $D_{Z1s}$, is set to $D_c$ to compensate for an over-drive region necessary for start-up. Where no such region is required, $D_{Z1s}$, can be equal to $D_i$. The end diameter of the final, or 8th in the illustrative embodiment, zone $D_{Z8e}$ is set to $D_f$, the final diameter of the yarn package.

Figure 7:
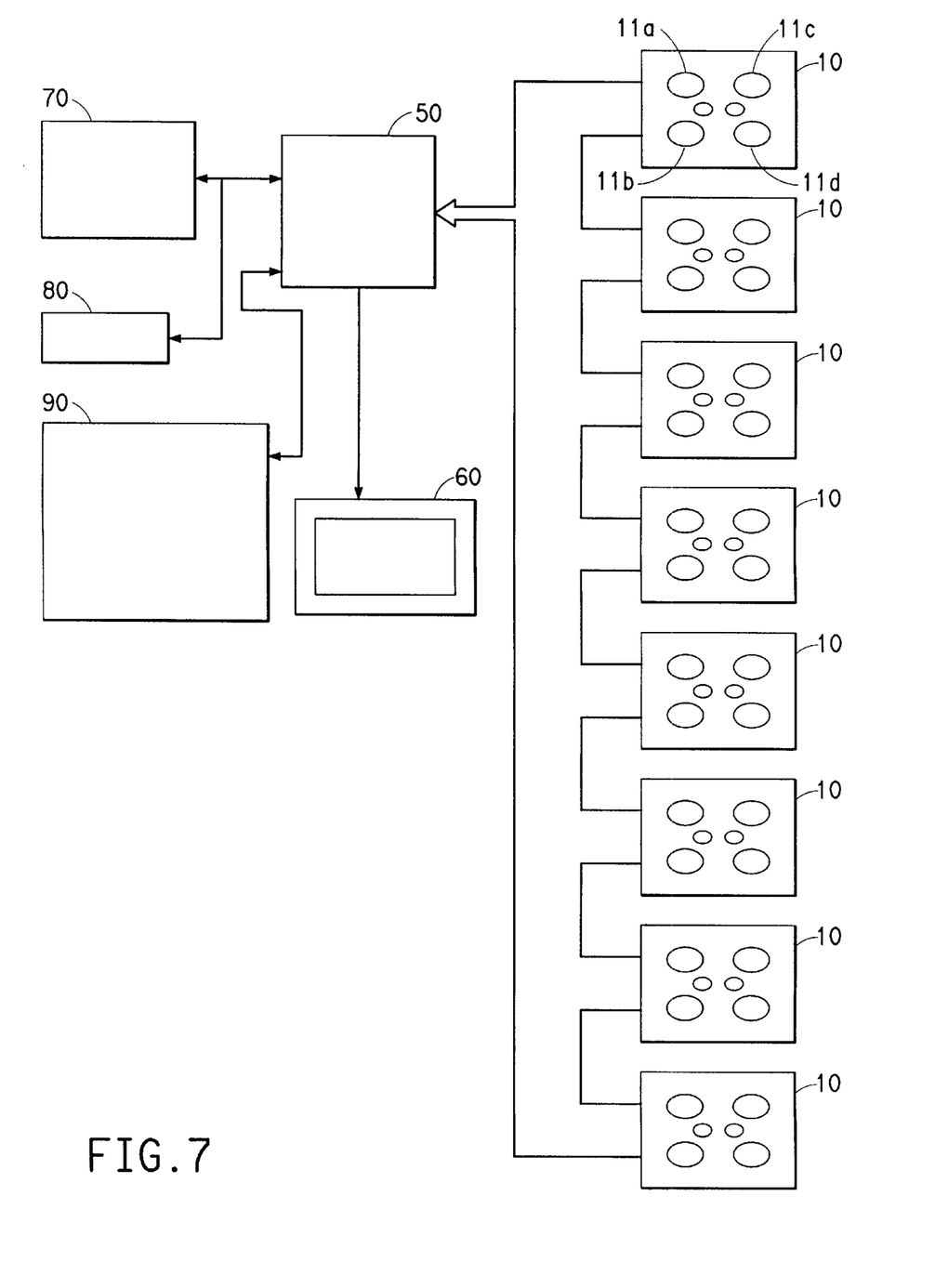
FIG. 7 is an illustrative implementation of one embodiment of the present invention.

FIG. 7 illustrates one implementation of the present invention according to the illustrative embodiment.

In the illustrative embodiment, eight winding apparatus 10 are electrically connected to a microprocessor based control device 50. The microprocessor device 50 will calculate denier measurements for particular zones for each package being wound at a position for up to eight positions. Although a personal computer ("PC") or any microprocessor based device, or other equivalent, can be used, for reasons of reliability, in the illustrative embodiment a dedicated programmable logic controller ("PLC") is used, specifically, the well known Allen-Bradley PLC-5.

The PLC 50 provides output to and receives input from an operator console 70 and a computer 90. The PLC 50 provides output to a monitor 60 and label printer 80.

The operator console 70, in the illustrated embodiment, is a PC allowing a system operator the capability of data entry and retrieval to and from PLC 50.

Figure 9:
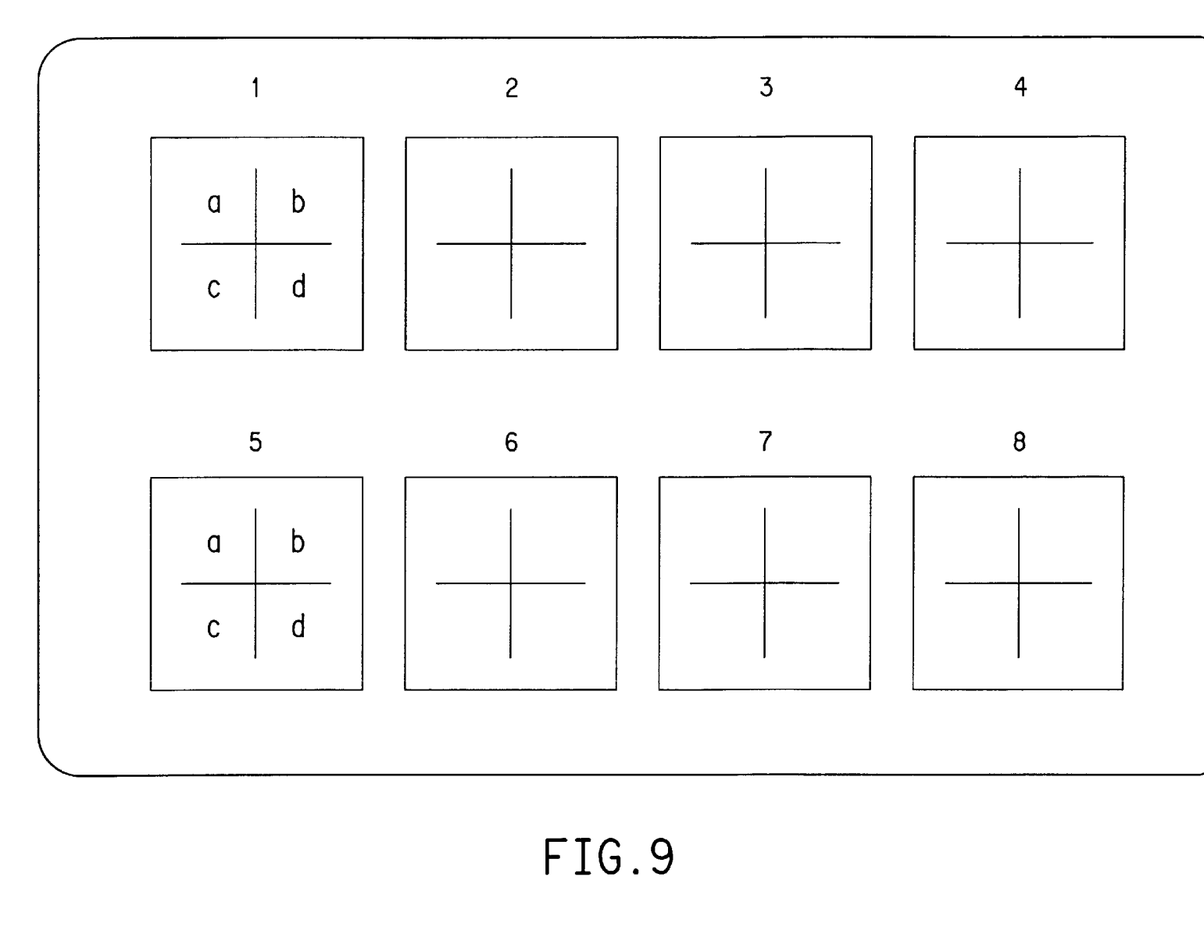
FIG. 9 is an illustration of the monitor display according to the one embodiment of the present invention.

The monitor 60, in the illustrated embodiment, is a dumb terminal which allows notification of an operator, by the PLC 50, of the status of the winding packages. In this embodiment, as shown in FIG. 9, a screen display is generated to show package display elements which indicates the status of each package a–d per position 1–8. Each package display element is, in the illustrative embodiment, a two state color display element where condition normal ("GREEN") or anomaly detected ("RED"). When the wind cycle progresses normally, as will be explained in detail below, the package display element remains green. When an out of tolerance condition is detected, the package element illuminates red, indicating to the operator that action is required for that position.

The label printer 80 will print a label for each yarn package when the package winding has stopped and the package is removed from the winding apparatus. Each label will have product identifying information, including grade/ quality designation. The information printed on each label is also stored in an archive database via computer 90.

Computer 90 in the illustrative embodiment is a Digital Equipment Corp. (DEC) VAX computer. Computer 90 performs several functions in the illustrative embodiment. Computer 90 can serve for example, as a data archive (i.e., database) to store denier history for future denier calculations, maintaining a history of information for all packages produced by threadline, package zone and position, including grading and other identifying information.

Two real-time measurements for each station 11a–11d at each package zone are used by PLC 50. These are: (1) the time required to wind a package from a pre-determined start diameter to a pre-determined end diameter; and (2) yarn package revolutions per minute (RPM) as a square wave pulse, measured by the fixed sensor 34 and encoder 36.

The time required to traverse a particular zone (i.e., to wind a package from a pre-determined start diameter to a pre-determined end diameter) is measured via a timer within the PLC, triggered by predetermined start and end diameters.

Figure 6B:
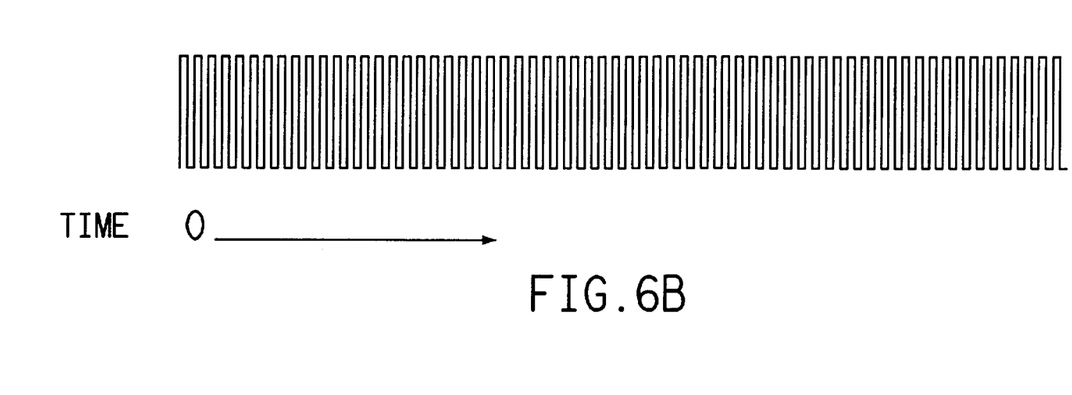
FIG. 6B illustrates the square wave pulse of the clock of the microprocessor device of the illustrative embodiment of the present invention.

Square wave pulses for each package being wound at each station, i.e., for each package zone, are provided to the PLC 50 by the sensor and encoder described above. The pulses, generated once per revolution of the spindle as the encoder 36 passes detector 34, are used to measure continuous package rotational speeds, as shown in FIG. 6A. The clock frequency pulse is shown in FIG. 6B. Using the following equation, the number of clock pulses N per revolution is determined:

$$N = \Delta t_{R1R2}(F_c)$$

where $F_c$=clock frequency

The continuous package rotational speeds are then determined as follows:

$$1/F(spindle) = (N)*(K_{F1})$$

or alternatively, $$RPM(spindle) = (K_{F2})/N$$

where:

I/F=inverse frequency, seconds

N=Number of 4 MHZ clock pulses during one spindle revolution as calculated above The conversion factors $K_{F1}$ and $K_{F2}$ are dependent upon the clock rate of PLC 50. The Allen Bradley PLC used in the illustrative embodiment has a 4MHz clock, necessitating factor values of $K_{F1}=6.25\times10^{-8}$, $K_{F2}=9.6\times10^{8}$. The dependency of the conversion factors upon clock rate will be understood by one of ordinary skill in the art.

Since the diameter (30, see FIG. 3) and rotational speed of the package driveroll 20 are precisely known and the package rotational speed is derived (as above), the diameter of the package being wound can be calculated by the well-known gear ratio as follows:

$$d2 = n1/n2 * d1$$

where:

d1=diameter of driveroll d2=(surface) diameter of package being wound n1=rotation speed of driveroll n2=rotation speed of package being wound These two inputs are fundamental to yarn package denier measurements.

With denier defined as linear density as follows, $$Denier = weight\ (in\ grams)/9000\ meters\ of\ yarn$$

the volume of yarn being measured can be determined by the continuous measurement of package rotational speeds which are used to calculate the package diameter in real time. As the package is surface driven by a driveroll of known diameter and rotational speed, the package rotational speed is measured and the diameter of the package being wound can be calculated by the gear ratio above.

Since the diameter of a package being wound is continuously calculated, the difference between two specified start and end diameters on a package defme an annular area, which, when projected over the length of the package, yields an annular volume. The weight of yarn enclosed by the annular volume yields a nominal package density:

$$W = (\pi)/4 * L * \rho * (de^2 - ds^2)$$

where:

W=Weight of denier sample

π=3.1416

L=Package length

ρ=Package nominal density $d_e$=Package diameter at end of denier zone $d_s$=Package diameter of start of denier zone A package diameter which defines the start of a denier measurement and a diameter which defines the end of a denier measurement can be developed by the relation:

$$d_e = d1 * n1/n_e$$
$$d_s = d1 * n1/n_s$$

where:

n=Package rotational speed at end of denier measurement $n_s$=Package rotational speed at start of denier measurement The inverse of package rotational speeds (n) is the inverse frequency, or the period (time) for, one spindle revolution. Therefore, the inverse frequency is:

$$t_e = 1/n_e$$
$$t_s = 1/n_s$$

where:

$t_e$=inverse frequency or time required for one package revolution at end of denier measurement zone $t_s$=inverse frequency or time required for one package revolution at start of denier measurement zone Combining the above:

$$W = (\pi)/4 * L * \rho * d1^2 * n1^2 * [t_e^2 - t_s^2]$$

The true yarn speed being wound on the package is determined as:

$$TYS = DR_{ypm}/Cos(\theta) = n1 * (\pi) * d1/Cos(\theta)$$

where:

TYS=True yarn speed of threadline being wound $DR_{ypm}$=Driveroll speed in yards per minute θ=Helix angle of threadline being wound on package Transformed per 9000 meter of yarn, with T=Time to wind an annular volume, and adding a calibration factor K and a unit conversion factor $K_c$, the final on-line denier, D, is calculated by the PLC as follows:

$$Denier = K * K_c/T * Cos(\theta) * L * \rho * DR_{ypm} * [t_e^2 - t_s^2]$$

In the illustrative embodiment, each PLC 50 has the throughput capacity to service 8 positions (i.e., 32 simultaneous yarn package windings). Electrical connection, shown in FIG. 7, for the analog rotational speed signals provided for each position to the PLC will be understood by one of ordinary skill in the art. For example, an analog-to-digital converter in the PLC is utilized in the illustrative embodiment to convert the incoming analog signals to digital quantities.

Figure 8A:
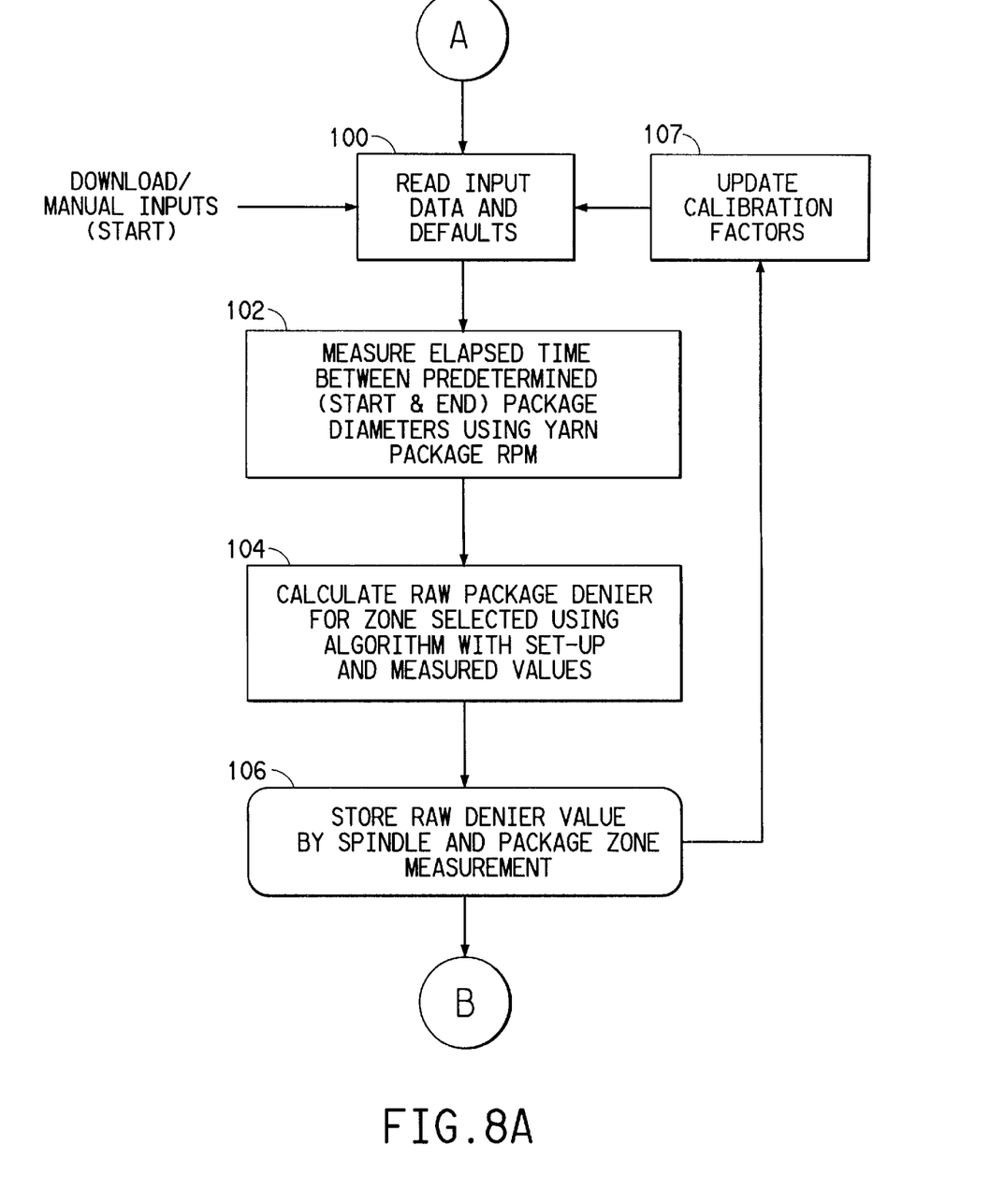
FIGS. 8A & 8B is a flow chart of the method according to the present invention.
Figure 8B:
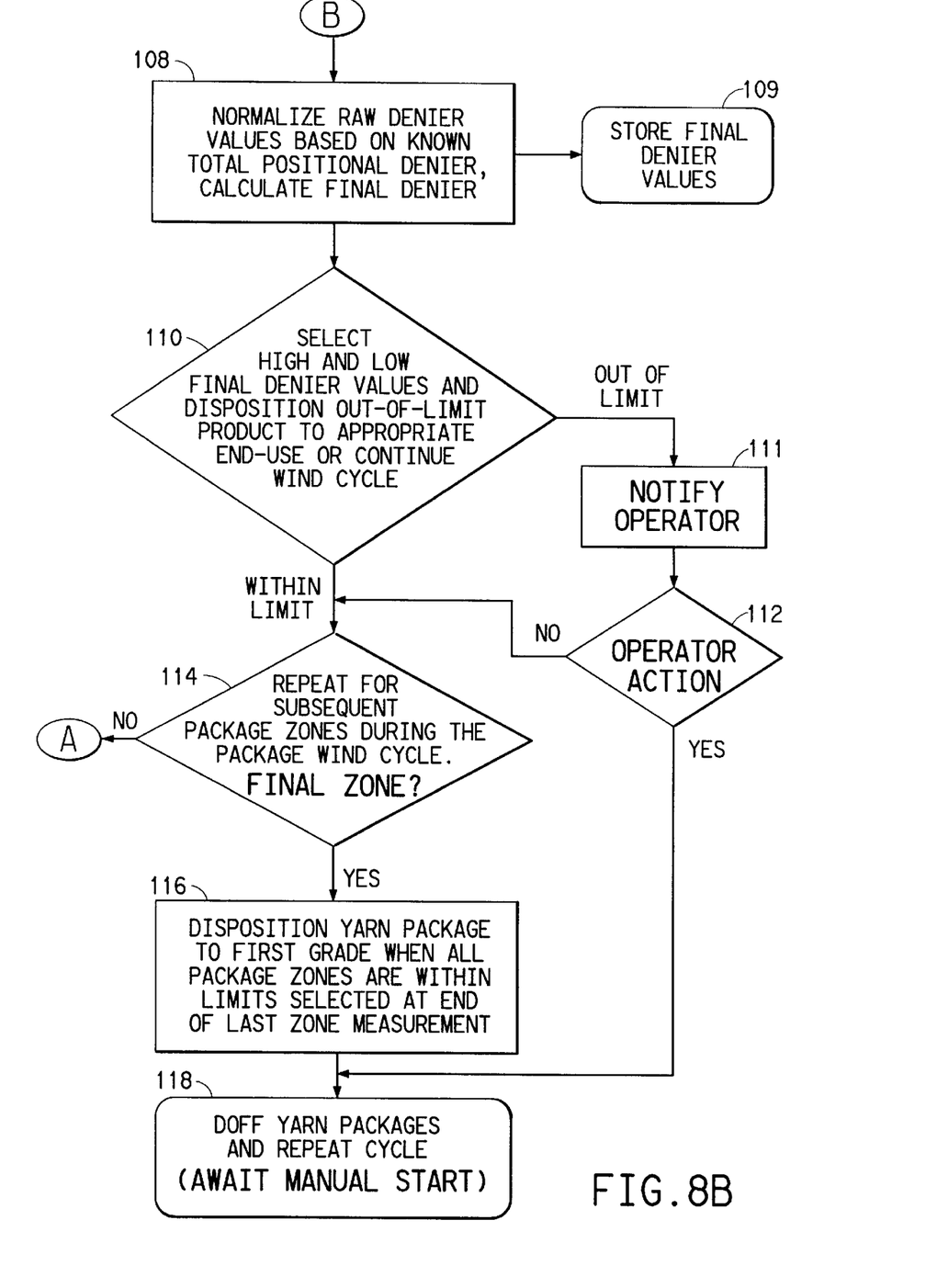

The PLC will be programmed appropriately with an algorithm, as will be understood by one of ordinary skill in the art, according to the flow chart set forth in FIGS. 8A and 8B.

With reference to FIGS. 8A and 8B, the winding process and the method of the present invention are started via input at step 100. It is in this step that initial default values are provided. A portion of the parameters use in the method of the present invention include known process, or starting operating condition, values which can be either manually entered upon start-up or when production changes occur via operator console 70, or, can be down-loaded from an electronic database stored in the mainframe computer 90. Starting operating condition values, for example, include start and end diameters for each radial zone and target or aim denier for yarn packages to be wound during that wind cycle.

In step 102, the start of a denier measurement for a selected radial zone begins when a predetermined package diameter is reached. The package diameter (or equivalent package rotational speed) at the beginning of the denier measurement is stored in the PLC and a timer, which measures to within 1/100 of a second, is started. The diameter of the package being wound is continuously checked until a predetermined final package diameter is reached. This signals the end of the denier measurement zone and thus, the start and end package diameters define the zone within the package which is being checked for denier. The end package diameter along with the start package diameter and time (seconds) between the package start and end diameters are stored.

In step 104, the measured values (from step 102), along with known downloaded process values, are used to calculate a raw denier value.

Raw package deniers are calculated for all yarn packages being wound at each station, e.g., in FIG. 1, each yarn package 12 at stations 11a, 11b, 11c and 11d. Raw denier values which are within a desired range of the denier target (or aim) are stored in a database. For the illustrative embodiment, the allowable range for values which can enter the database is set to ±4.2%. A calibration factor (K) is maintained for each zone for each spindle. These raw denier values for each package zone on each spindle are used to provide a data base for updating calibration factors on a continuous 24 hour routine. The calibration factor accounts for drifts due to winding dynamics which primarily affect nominal package density.

A preliminary (raw) package denier, D, is calculated as follows:

$$D = K * K_e/T * cosine(\theta) * L * \rho_n * DR_{ypm} * (t_e^2 t_s^2)$$

where;

K=calibration factor $K_e$=a constant (unit conversion factor)

T=sampling time in seconds

θ=package wind helix angle in degrees

L=package length in inches $\rho_n$=nominal package density in pounds per cubic inch $DR_{ypm}$=wind-up drive-roll speed in yards per minute $te^2$=square of pulse length at end (te) of sampling period in ms.

$ts^2$=square of pulse length at start (ts) of sampling period in ms.

The ratio of the total preliminary calculated deniers to known total positional package deniers is used to refine the nominal package density $\rho_n$ to a current package density $\rho_e$ for a particular spinning position at that point in time. The final package denier will be recalculated (normalized) using the refined positional package density.

The final package denier is calculated in step 108. The total denier for a position (summed deniers for all packages) is controlled by precision meter pump(s) (one pump per spinning position) which supply polymer which becomes, during spinning, the yarn to be wound. The (positional) total denier is maintained by off-line measurement methods and is used to prorate raw denier values into final denier measurements. This factor provides a small immediate calibration for short term (<24 hours) spinning dynamics.

Addition of calibration factor K and unit conversion/ constants factor $K_e$ to the preliminary denier calculation equation yields the final denier calculation equation.

$$Denier = K * K_e/T * Cos(\theta) * L * \rho * DR_{ypm} * [t_e^2 - t_s^2]$$

The calibration factor K is updated according to the following.

$$K2 = K1 + P * [(DA/RCDA*K1) - K1]$$

where:

K1=existing K-value, (use default of 1.0 on first pass)
K2=new K-value
P=Damping factor
DA=denier target (or aim)
RCDA=Raw calculated denier average (from last 24 hour raw denier database)

The final denier values are stored in step 109 by the PLC.

Once the final denier for each package check zone has been calculated, the highest and lowest final denier values are compared. If these values are within the predetermine tolerance, no missing/gained filament is deemed detected. Each package is dispositioned according to predetermined disposition package tolerance limits in step 110.

Where the highest and lowest final denier values are not within the predetermine tolerance, a missing/gained filament is deemed detected and the flow proceeds to step 111 to issue a notification to the operator (via monitor 60 in FIG. 7), at which point, the operator is instructed to take prescribed remedial action such as terminating the wind-cycle.

Where no out of tolerance condition is detected (step 110) or if the operator does not take action (step 112), the flow continues to step 114 to process subsequent radial package zones. If an out of tolerance condition was detected and the operator has not taken action, the out of tolerance event will be stored by the PLC for later use in providing the proper disposition code (on the label) and proper yarn disposition (see step 116 below). If there are remaining zones, the flow continues to A at step 100.

If all designated zones have been processed, i.e., there are no remaining zones, the yarn package is dispositioned as appropriate in step 116. For example, if all measured zones were within limits, the yarn package will be dispositioned as first grade and the label printer (80 in FIG. 7) will be commanded by the PLC to print a first grade label for that package. If one measured zone was out of limits and the operator had not taken action, the yarn package will be dispositioned as degraded product and the label printer will be commanded to print such a label for that package. The grade information for each package is stored in a database via a mainframe (90 in FIG. 7).

In step 118, the operator will take the completed package off the winding apparatus (i.e., the operator will "doff the yarn packages"). The algorithm will then await a manual restart for a new winding cycle.

A sample calculation utilizing 3 radial zones to facilitate explanation will aid in an understanding of the present invention.

Typical start/end package diameters are selected for a 27 pound package as shown in Table I.

TABLE I

Start/end package diameters selected for denier measurements of a 27 pound yarn package.

| Measurement Zone | Start Diameter, inches | End Diameter, inches |
|---|---|---|
| 1 | 4.38 | 5.38 |
| 2 | 7.13 | 8.38 |
| 3 | 9.38 | 10.38 |

TABLE II

Typical measured and other process setup parameters used in measuring 850 (target or aim) denier product

| Variable Name | Measured Value | Process Setup | Calculated Value |
|---|---|---|---|
| T | 285 | | |
| K | | | 0.999 |
| $K_c$ | | 7.674 | |
| θ | | 9.6 | |
| L | | 15 | |
| ρ | | 0.03 | |
| $DR_{ypm}$ | 2808 | | |
| te | 11.9332 | | |
| ts | 10.8147 | | |

As indicated above, the preliminary denier measurement is as follows:

$$Denier = K * K_e/T * Cos(\theta) * L * \rho * DR_{ypm} * (t_e^2 - t_s^2)$$

Substituting Table II parameters into the preliminary (raw) denier equation:

$$Denier = 0.999/285 * 7.674 * Cos(9.6) * 15 * 0.03 * 2808 * [11.9332^2 - 10.8147^2] = 853$$

The calibration factor K2 is updated according to the following equation.

$$K2 = K1 + P * [(DA/RCDA*K1) - K1]$$

where: Typical Value

K1=existing K-value 1.002
K2=new K-value
P=Damping factor 0.6
DA=denier target (or aim) 850
RCDA=Raw calculated denier average 854 (from last 24 hour raw denier database)

Thus K2=1.002+0.6×[(850/854*854)−1.002]=0.999

The final denier is then determined as shown in Table m.

TABLE III

Prorating raw to final deniers for single position of
four 850 denier packages
Denier target (or aim) = 850
Total positional denier = 4 × 850 = 3400
Sum of positional raw deniers = 853 + 845 + 845 + 847 = 3390
Prorating factor = Total positional denier/sum of raw deniers =
3400/3390 = 1.0029

| Station | Denier Zone | Raw Denier | Final Denier = Raw denier value*Prorating factor |
|---------|-------------|------------|--------------------------------------------------|
| 11a     | Z1          | 853        | 853 × 1.0029 = 855                               |
| 11b     | Z1          | 845        | 845 × 1.0029 = 847                               |
| 11c     | Z1          | 845        | 847 × 1.0029 = 849                               |
| 11d     | Z1          | 847        | 849 × 1.0029 = 851                               |

(It will be appreciated by one skilled in the art that multiplying the prorating factor by raw denier is equivalent to multiplying the nominal density by the prorating factor and again substituting into the final denier equation.)

The highest and lowest final denier values are compared and, in the sample calculation, found to be within the 3.0% tolerance. As such, no missing/gained filament is deemed detected and these package will be dispositioned as first grade yarn.

Although the winding apparatus 10 of the illustrative embodiment has been described as having 4 stations capable of winding 4 yarn packages simultaneously, the present invention is none the less applicable where any number of packages are wound.

The foregoing description of specific embodiments of the present invention is intended to be merely an example of the inventive features of the present invention and many modifications will be possible without departing from the spirit of the invention or the scope of the appended claims.

I claim:

1. A method for using a microprocessor to monitor linear density, on-line, of at least one yarn package formed through winding of multifilamentary yarns during a wind cycle on a first winding position at a winding apparatus, said apparatus capable of winding a plurality of said at least one yarn package simultaneously at a plurality of winding positions, the first winding position being one of said winding positions, said method comprising the steps of:

inputting predetermined process parameters, including a tolerance range and at least one diameter range;

inputting rotation speed of each said at least one yarn package;

deriving a time interval required to wind said at least one yarn package through said at least one diameter range for each said at least one yarn package;

calculating a denier value for said at least one yarn package through one of said at least one diameter range using said corresponding rotation speed, said corresponding time interval and said predetermined process parameters;

determining whether said calculated denier value is within said tolerance range for said at least one yarn package through one of said at least one diameter range; and repetitively performing for a remainder of said at least one diameter range throughout said wind cycle, said steps of inputting rotation speed, deriving a time interval, calculating a denier value, and determining whether said calculated denier value is within said tolerance range.

2. The method of claim 1 further comprising displaying results of said determining whether said calculated denier value is within said tolerance range for said at least one yarn package for each said at least one diameter range.

3. The method of claim 1 further comprising:

maintaining a history of said calculated denier value for said at least one yarn package for each said at least one diameter range for each of said winding positions by storing each said calculated denier value in a database; and updating for said at least one yarn package for each said at least one diameter range said denier value based on said stored value via an adjustable calibration factor.

4. The method of claim 1 wherein said predetermined process parameters further include:

a unit conversion factor;

an initial value for an adjustable calibration factor;

yarn package wind cycle time period; and yarn package nominal density.

5. The method of claim 1 wherein said calculating step includes the steps of:

calculating length of yarn wound onto said at least one yarn package for each said at least one diameter range during said corresponding time interval;

calculating an annular volume for each said at least one yarn package for each said at least one diameter range;

converting each said annular volume into weight measurement for each said at least one yarn package for each said at least one diameter range;

calculating raw linear density for each said length of yarn wound from each said weight measurement; and converting said raw linear density to a normalized linear density for each said at least one yarn package for each said at least one diameter range.

6. The method according to claim 5 wherein said step of determining whether said calculated denier value is within said tolerance range includes:

comparing said normalized linear density per each said at least one yarn package for each said at least one diameter range and identifying a maximum value and a minimum value of said normalized linear density per each said at least one yarn package for each said at least one diameter range and storing said normalized density value including said maximum value and said minimum value for each said at least one diameter range in each said at least one yarn package.

7. The method according to claim 6 further comprising the steps of:

dispositioning one of said at least one yarn package for release when said maximum value and said minimum value of said normalized linear density of each said at least one diameter range in said at least one yarn package is within said tolerance range; and initiating spinning position corrective action when said maximum value and said minimum value of said normalized linear density of any one of said at least one diameter range in said at least one yarn package is not within said tolerance range.

8. The method of claim 7 wherein said step of initiating corrective action includes displaying said maximum value and said minimum value which are not within said tolerance range.

9. A method for using a microprocessor to monitor linear density, on-line, of at least one yarn package formed through winding of multifilamentary yarns during a wind cycle on a first winding position at a winding apparatus, said apparatus capable of winding a plurality of said at least one yarn package simultaneously at a plurality of winding positions, the first winding position being one of said winding positions, said method comprising the steps of:

(a) inputting predetermined process parameters, including a tolerance range, at least one diameter range, a unit conversion factor, an initial value for an adjustable calibration factor, linear density per each of said winding positions, yarn package wind cycle time period, and yarn package nominal density;

(b) inputting rotation speed of each said at least one yarn package;

(c) deriving a time interval required to wind said at least one yarn package through said at least one diameter range for each said at least one yarn package;

(d) calculating length of yarn wound onto said at least one yarn package for each said at least one diameter range during said corresponding time interval;

(e) calculating an annular volume for each said at least one yarn package for each said at least one diameter range;

(f) converting each said annular volume into weight measurement for each said at least one yarn package for each said at least one diameter range;

(g) calculating raw denier for each said length of yarn wound from each said weight measurement;

(h) normalizing said raw denier to a final denier for each said at least one yarn package for each said at least one diameter range;

(i) maintaining a history of said final denier for said at least one yarn package for each said at least one diameter range for each of said winding positions by storing each said final denier in a database;

(j) updating for said at least one yarn package for each said at least one diameter range said raw denier based on said stored final denier via said adjustable calibration factor;

(k) determining whether said final denier is within said tolerance range for said at least one yarn package through one of said at least one diameter range and identifying a maximum value and a minimum value of said final denier per each said at least one yarn package for each said at least one diameter range and storing said final denier including said maximum value and said minimum value for each said at least one diameter range in each said at least one yarn package;

(l) displaying results of said determining whether said final denier is within said tolerance range for said at least one yarn package for each said at least one diameter range;

(m) repetitively performing steps (b) through (l) for a remainder of said at least one diameter range throughout said wind cycle;

(n) initiating spinning position corrective action whenever said maximum value and said minimum value of said final denier of any one of said at least one diameter range in said at least one yarn package is not within said tolerance range; and (o) dispositioning each said at least one yarn package for release upon completion of said repetitively performing step when all corresponding results of said determining step are within said tolerance range.

10. An apparatus for determining linear density, on-line, of at least one yarn package formed on a winding apparatus through winding of multifilamentary yarns from a spinning position, comprising:

a microprocessor based device;

a yarn package diameter measurement device for measuring diameter of each said at least one yarn package;

a rotational speed sensor for sensing rotational speed of each said at least one yarn package, said sensor for providing a sensed speed signal; and a timer for measuring time required to traverse a region defined by a start and end diameter measured by said yarn package diameter measurement device, said timer for providing a timing signal corresponding to said measured time, wherein said speed signal and said timing signal are adapted to be provided to said microprocessor based device for on-line, real-time calculation and monitoring of said linear density of said at least one yarn package, said calculation and said monitoring being on-line and real-time with respect to the spinning position.

11. The apparatus of claim 10 further comprising a display to provide real-time display of said calculated linear density.

12. The apparatus of claim 10 further comprising a printer to print package labeling based on said calculated linear density.

13. The apparatus of claim 12 further comprising a computer for storing information printed on said package labeling.

14. The apparatus of claim 10 further comprising an input device for inputting process parameters to said microprocessor based device, said process parameters to be used for said calculation.

15. The apparatus of claim 14 wherein said input device is a computer.

16. The apparatus of claim 10 further comprising a computer for providing a database for storing said calculated linear density and maintaining a history of said calculated linear density.

17. The apparatus of claim 16 wherein said history of said calculated linear density is used for said calculation of said linear density.

18. The apparatus of claim 10 wherein said timer is implemented in said microprocessor based device.

19. An apparatus for determining linear density, on-line, of at least one yarn package formed on a winding apparatus through winding of multifilamentary yarns from a spinning position, comprising:

a microprocessor based device;

an input device to allow input of process parameters to said microprocessor based device;

a yarn package diameter measurement device for measuring diameter of each said at least one yarn package;

a rotational speed sensor for sensing rotational speed of each said at least one yarn package and providing a sensed speed signal;

a timer for providing a timing signal corresponding to a time required to traverse a region defined by start and end yarn package diameters measured by said yarn package diameter measurement device;

a first computer for providing a database for storing calculated linear density values and maintaining a history of said calculated linear density values; and a display, wherein (1) said speed signal and said timing signal are adapted to be provided to said microprocessor based device for on-line, real-time calculation of said linear density values of said at least one yarn package based on said history of said calculated linear density values and said process parameters, (2) said calculated linear density values are adapted to be compared on-line, in real-time to a tolerance range, (3) results of said comparison are adapted to be displayed on said display to provide real-time display of said calculated linear density values, and (4) on-line, real-time actions in (1)–(3) are on-line and real-time with respect to the spinning position.

20. The apparatus of claim 19 wherein said input device is a computer.

21. The apparatus of claim 19 wherein said timer is implemented in said microprocessor based device.

22. The apparatus of claim 19 wherein said apparatus further comprises:

a printer to print package labeling based on said calculated linear density values.

23. The apparatus of claim 22 wherein information to be printed on said package labeling is also stored in said first computer.

* * * * *